United States Patent [19]

Matsunaga et al.

[11] Patent Number: 4,751,074

[45] Date of Patent: Jun. 14, 1988

[54] HAIR RINSE COMPOSITION

[75] Inventors: Kinjiro Matsunaga, Saitama; Takeo Okumura, Sakura; Sachio Naito, Tokyo; Rikio Tsushima, Wakayama, all of Japan

[73] Assignee: Kao Soap Co., Ltd., Tokyo, Japan

[21] Appl. No.: 818,066

[22] Filed: Jan. 13, 1986

Related U.S. Application Data

[63] Continuation of Ser. No. 561,797, Dec. 15, 1983, abandoned.

[30] Foreign Application Priority Data

Nov. 17, 1980 [JP] Japan .................. 55-161599

[51] Int. Cl.$^4$ .................. A61K 7/06; A61K 7/08
[52] U.S. Cl. .................. 424/70; 514/880
[58] Field of Search .................. 424/70

[56] References Cited

U.S. PATENT DOCUMENTS 4,390,525 6/1983 Yashioka .................. 424/359

FOREIGN PATENT DOCUMENTS 0089212 7/1980 Japan .................. 424/70

OTHER PUBLICATIONS

Ash, a Formulary of Cosmetic Preparations, 1977, pp. 126 & 127.

Primary Examiner—Dale R. Ore
Attorney, Agent, or Firm—Oblon, Fisher, Spivak, McClelland & Maier

[57] ABSTRACT

A hair rinse composition which comprises at least one cationic surface active agent and a decomposition derivative of a keratin material which have been dissolved or dispersed in a suitable solvent. The decomposition derivative is a member selected from hydrolysates of keratin material, alkali salts of decomposition products obtained by oxidation of keratin material, alkali salts of derivatives at a thiol group of decomposition products obtained by reduction of keratin material and a mixture thereof.

2 Claims, No Drawings

HAIR RINSE COMPOSITION

This application is a continuation of application Ser. No. 561,797, filed Dec. 15, 1983, now abandoned.

BACKGROUND OF THE INVENTION

1. Field of the Invention:

This invention relates to a hair rinse and more particularly, to a hair rinse composition which comprises cationic surface active agents and a specific type of decomposition derivatives of keratin material and which shows an excellent hair conditioning effect.

2. Description of the Prior Art:

On washing of hair with shampoos comprised mainly of anionic surface active agents to remove stains from hair, it will be found that oil protecting the hair surface as well as the stains is removed. The removal of the oil from the surface of hair results in a loss of flexibility of hair and also in unglossy and hard-to-comb hair, showing a tendency of causing the hair to be damaged, split-ends and broken hairs.

In order to prevent these troubles from occurring, to give a hair-conditioning effect or impart to the hair flexibility, softness, and smoothness, and to improve the easiness for combing, hair rinses have been conventionally employed.

Known hair rinses are fundamentally made of quaternary ammonium salts as a cationic surface active agent serving to impart the softness and smoothness to hair and an oil component such as liquid paraffin, higher alcohols or the like for supplementing an oil to hair to form an oil film on the surface of hair so that the hair is imparted with gloss and is reduced in damage of hair owing to the friction with brush, comb or the like and prevented from being split at the ends thereof and broken.

However, the quaternary ammonium salts have no capability of stably emulsifying and dispersing oil components in amounts sufficient to show such effects as mentioned above and thus the hair rinses become unstable. Where nonionic surface active agents are added to improve the above, there is a disadvantage that the inherent rinsing effect lowers. Then, there have been proposed stable hair rinses in which there are used instead of the oil components anionic surface active agents, anionic polymer compounds, cationic polymeric compounds, and hydrolysates of collagen. However, these rinses are not satisfactory yet.

SUMMARY OF THE INVENTION

It is accordingly an object of the present invention to provide a hair rinse composition which shows excellent hair conditioning effects.

It is another object of the invention to provide a hair rinse composition which can impart softness, smoothness and ease in combing to hair while preventing formation of split-ends and broken hair.

It is a further object of the present invention to provide a hair rinse composition which makes use of a specific type of keratin derivatives.

The above objects can be achieved, according to the invention, by a hair rinse composition which comprises at least one cationic surface active agent and a specific type of one or more of decomposition derivatives of keratin material. The decomposition derivatives of keratin material to be used in the practice of the invention are (1) hydrolysates of keratin materials, (2) alkali salts of decomposition products obtained by oxidation of keratin materials, (3) alkali salts of derivatives at the thiol group of decomposition products obtained by reduction of keratin materials (which derivatives being hereinafter referred to simply as reduction derivatives of keratin material), and a mixture thereof. These rinse components are usually dissolved or dispersed in suitable solvents or media in predetermined amounts defined hereinafter.

DETAILED DESCRIPTION AND EMBODIMENTS OF THE INVENTION

The cationic surface active agents to be used in the present invention are not critical and may be all the agents which are usable in ordinary hair rinses and are preferably quaternary ammonium salts represented by the general formula (I)

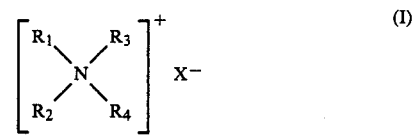

(in which one or two of $R_1$, $R_2$, $R_3$ and $R_4$ represent a long chain alkyl group or long chain hydroxyalkyl group having 8–20 carbon atoms, the other represent an alkyl group or hydroxyalkyl group having 1–3 carbon atoms, or a benzyl group, and X represents a halogen atom or an alkylsulfate having 1–2 carbon atoms). Preferable examples of the quaternary ammonium salts include distearyldimethylammonium chloride, stearyltrimethylammonium methosulfate, stearyltrimethylammonium chloride, stearyldimethylbenzylammonium chloride, lauryldiethylbenzylammmonium chloride, lauryltrimethylammonium bromide, distearylmethylhydroxymethylammonium chloride, cetyltrimethylammonium chloride and the like.

The decomposition derivatives of keratin to be used in the present invention can be prepared by hydrolyzing keratin materials, decomposing keratin materials by oxidation and converting the decomposed materials into their alkali salts, or decomposing keratin materials by reduction, chemically modifying the thiol group thereof to give derivatives and then converting them into corresponding alkali salts.

The starting keratin materials include, for example, animal hair, human hair feathers, claw, horn, hoof, scale and the like, among which wool, hair and feather are preferably used. These keratin materials may be subjected to oxidation or reduction reaction as they are but if necessary, they may be cut or reduced into pieces having a suitable size, or subjected to pretreatments such as washing and defatting.

The decomposition of the kerain materials can be conducted by any of the following methods.

(1) Hydrolysis

1. Hydrolysis with Acid

Mentioned as acid are, for example, inorganic acids such as hydrochloric acid, sulfuric acid, phosphoric acid, nitric acid, hydrobromic acid and the like and organic acids such as acetic acid, formic acid, oxalic acid and the like. These acids are generally employed at a concentration of 3–85% and it is desirable that the hydrolysis is conducted at a pH of 4 or below. The reaction temperature is preferably in the range of 40°–100° C. though it may be raised up to 160° C. under pressure. The reaction time is conveniently in the range of 2–24 hours. The reaction product may be used as it is after neutralization with alkalis such as sodium hydoxide, sodium carbonate and ammonia or may be used after purification such as by gel filtration and ion exchange resins.

The product obtained by the hydrolysis with acid merely undergoes the hydrolysis at the polypeptide chain of keratin without involving any other changes, so that it shows better results than ones obtained by hydrolysis with alkali.

2. Hydrolysis with Alkali

As alkalis there are used inorganic alkalis such as sodium hydroxide, potassium hydroxide, lithium hydroxide, barium hydroxide, sodium carbonate, potassium carbonate, lithium carbonate, sodium silicate, borax and the like. These are ordinarily used at a concentration of 1–20%. Larger amounts than as required are unfavorable since the solution of hydrolysate is turned brown to black in color.

The reaction is preferably conducted at a temperature of room temperature to 100° C. for a time of 30 minutes to 24 hours. Care should be taken not to make the temperature higher and the reaction time longer than required. The hydrolysis with alkali has an advantage that the reaction process can be visibly observed because the hydrolysate of keratin dissolves in the reaction mixture. The reaction is completed at the time when the reaction mixture has been turned into a homogeneous solution.

3. Hydrolysis with Enzyme

Examples of enzymes to be employed include acidic proteinases such as pepsin, protease A, protease B and the like, and neutral proteinases such as papain, bromelain, thermolysin, trypsin, and chymotrypsin and the like. The pH of the hydrolysis should preferably be controlled to be in the range of 1–3 for the acidic proteinases such as pepsin and in the range of 5–8 for the neutral proteinases such as papain. It is convenient that the pH is properly adjusted by the use of an ammonium acetate/ammonia buffer solution, a phosphoric acid buffer solution and the like buffer solutions. The reaction temperature is favorably in the range of 30°–45° C. and the reaction time is ordinarily in the range of 3–24 hours.

With the hydrolysis with enzymes, the molecular weight of hydrolysate is greatly influenced by the amount of enzyme, reaction temperature and reaction time. Accordingly, in order to obtain a keratin hydrolysate with an intended molecular weight, it is necessary to check by the gel filtration technique a distribution of the molecular weight of hydrolysate in relation to variations in the amount of enzyme, reaction temperature and reaction time so as to empirically determine the optimum conditions.

The hydrolysates obtained from enzymes show a narrower distribution of molecular weight than hydrolysates obtained from acids or alkalis and contain smaller amounts of free amino acids, thus being more favorable for use in cosmetics.

The hydrolysates obtained by these hydrolysis reactions should preferably have an average molecular weight of from 200 to 5,000.

This is because the adsorbability of the decomposition product of keratin on hair depends on the molecular weight thereof and a product with a molecular weight of about 1000 is most ready to adsorb on hair but those having an average molecular weight larger than 5,000 scarecely adsorb on hair. The disulfide bonds in the keratin decomposition derivative should preferably be left in amounts as large as possible. To this end, it is needed to use a keratin material of high purity and to effect the hydrolysis under mild conditions.

(2) Oxidation Reaction

The oxidation of keratin material is feasible by any of methods known per se (N. H. Leon; Textile Progress, Vol. 7, page 1 (1975) Oxidizing agents are preferably of the type which may be either organic or inorganic but acts electrophilically on the disulfide bond (S-S bond) in the keratin structure. Examples of the oxidizing agents include organic peradids, inorganic peroxo acids or their salts, permanganic acid or its salts, chromic acid or the related compounds, halogens, peroxides, oxyacids or their salts and the like, among which the organic peracids such as peracetic acid, performic acid and perbenzoic acid are most preferable.

The oxidation reaction is conducted in liquid media using oxidizing agents in excess with respect to the disulfide bonds in the keratin material, ordinarily in amounts of over two equivalents or more, preferably 4–10 equivalents, of the disulfide bonds. The reaction is feasible under acidic or alkaline conditions and is preferably conducted under acidic and particularly weakly acidic conditions. The reaction temperature and pressure are varied depending on the types of the oxidizing agent and keratin material and are not critical. In general, room temperature is sufficient but, if necessary, heat may be applied. An atmospheric pressure is sufficient but the reaction may be conducted under reduced pressure or under pressure.

By this, the disulfide bond of keratin material is oxidized into sulfonic acid.

(3) Reduction Reaction and Chemical Modification Reaction

Reducing agents employed for reducing keratin materials are preferably organic or inorganic reducing agents of the type which serves to cleave the disulfide bond in the keratin structure into a thiolgroup (—SH) and generally nucleophilically acts on the disulfide bond. Examples of the reducing agents include organic reducing agents such as mercaptoethanol, thioglycollic acid, benzylmercaptan, 1,4-dithiothreitol, tributylphosphine and the like, and inorganic reducing agents such as sodium hydrogensulfite, sulfides such as sodium hydrosulfide, metallic hydrides such as lithium aluminium hydride.

The amount of the reducing agent is usually in the range of 2–10 equivalents of the disulfide bonds in keratin material. The pH of the reaction system is in the range of 2–12, preferably 6–11. Outside the range, the hydrolysis undesirably takes place at the same time. Room temperature is sufficient for the reaction but heat may be applied to shorten the reaction time. The reaction time is ordinarily in the range of 2–3 hours or more. Since the thiol group produced by the reduction is required not to be substantially oxidized, the reduction operation should conveniently be carried out in an atmosphere of inert gas to give good results.

The decomposition product obtained by the reduction of keratin material is then chemically modified at the thiol group thereof to obtain a derivative thereof. The derivatives at the thiol group include:

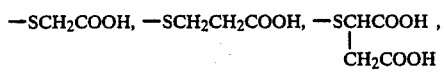

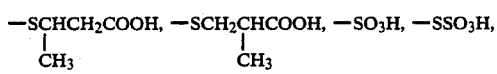

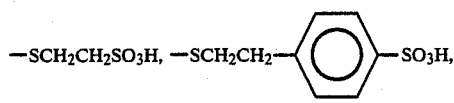

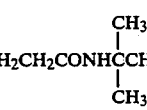 among which 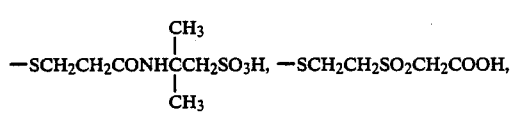 are preferable.

The chemical modification of the thiol group is known per se and can be conducted, for example, based on procedures known from N. H. Leon; Textile Progress, Vol. 7, page 1 (1975), "Yuki Ioo Kagobutsu (Organic Sulfur Compounds)" written by Shigeru Ooba and published by Kagaku Dojin (1968) and "Kobunshi Jikkengaku Koza" written by Masami Oku, Vol. 12, Kyoritsu Shuppan (1957). Typical methods are shown below.

1. Method utilizing the nucleophilic substitution reaction of SH group $$K-SH + R-L \rightarrow K-S-R + HL$$

(in which K represents a residue of keratin compound, R represents a chemically modifying group to be introduced, and L represents an leaving atom or group such as a halogen atom or an acid residue). Compounds reacting by this method include, for example, halogen compounds such as iodoacetic acid, bromoacetic acid, chloroacetic acid and the like.

2. Method utilizing the nucleophilic addition reaction of SH group with a double bond existing between carbon atoms

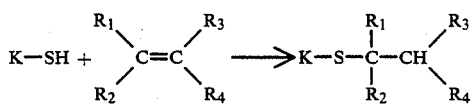

(in which at least one of $R_1$, $R_2$, $R_3$ and $R_4$ represents a carboxyl group or sulfonic acid group and the other represent an alkyl group or hydrogen atom, and K has the same meaning as defined hereinbefore). Compounds reacting by this method include, for example, acrylic acid, methacrylic acid, crotonic acid, maleic acid, fumaric acid, vinyl carboxymethylsulfone, vinylsulfonic acid, styrenesulfonic acid, 2-acrylamido-2-methylpropanesulfonic acid and the like.

3. Method using a substitution reaction between SH group and sulfite compound

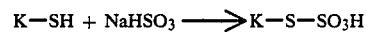

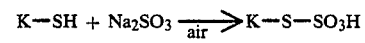

(in which K has the same meaning as defined above).

4. Method of oxidizing SH group into sulfonic acid group

(in which K has the same meaning as defined hereinbefore). The oxidizing agents used in this reaction include, for example, halogens, permanganates, and the like.

Alkali salts of the decomposition product obtained by oxidation of keratin material and reduction derivatives of keratin material include inorganic alkali metal salts such as sodium, potassium and the like, ammonium salts, and salts with organic bases such as ethanolamine, diethanolamine, triethanolamine, 2-amino-2-methylpropanol, aminomercaptopropanediol, triisopropanolamine, glycine, histidine, alginine and the like. These salts may be prepared separately and then added to a hair rinse. Alternatively, the oxidation decomposition product of keratin material or reduction derivative of keratin material and alkaline materials may be added to a hair rinse in which they are formed into a salt thereof. Examples of the alkaline materials include sodium hydroxide, potassium hydroxide, aqueous ammonia, ethanolamine, diethanolamine, triethanolamine, 2-amino-2-methylpropanol, aminomethylmercaptopropanediol, triisopropanolamine, glycine, arginine, histidine and the like. Preferably, the alkaline materials are added in an amount of 0.1-8 equivalents of the carboxyl group and sulfonic acid group in the oxidation decomposition product or reduction derivative of keratin material.

The hair rinse composition according to the invention is prepared by mixing 0.01-10 wt % (hereinafter referred to simply as %), preferably 0.2-5%, of one or more cationic active agents and 0.01-10%, preferably 0.1-5%, of one or more of decomposition derivatives of keratin material, and then dissolving or dispersing the mixture in a suitable solvent such as water, ethylene glycol, propylene glycol or the like.

Less amounts than 0.01% of the cationic active agent are unfavorable since its effect cannot be satisfactorily shown, whereas larger amounts are also unfavorable since the viscosity of the system becomes high, making it difficult to impart suitable fluidity to the composition. On the other hand, where the decomposition derivatives of keratin material are added in the amounts larger than 10%, hair undesirably becomes sticky under conditions of high humidity. If desired, higher alcohols, lanolin oil, esters, liquid paraffin, higher fatty acids, oils such as silicone oil, bactericides, perfumes and the like may be suitably added to the hair rinse composition according to the invention.

The present invention are particularly described by way of references and examples.

REFERENCE 1

Preparation of oxidation decomposition derivatives of keratin materials:

(a) Ten grams of wool fibers were immersed in 700 g of 8% aqueous peracetic acid solution at room temperature for 1 day for the oxidation reaction. The resulting oxidized wool was filtered and washed with water, and then immersed in 700 g of a 0.1N ammoniacal solution at room temperature for 1 day, permitting about 90% of the wool to dissolve in the ammoniacal solution. About 1 g of the insoluble matters were removed by filtration and the aqueous ammoniacal solution of keratose to be an oxidized decomposition product of wool keratin was admixed with 2N hydrochloric acid to adjust pH to 4.0, whereupon α-keratose was settled as a precipitate. This precipitate was filtered, washed with acetone and dried to obtain 5.4 g of α-keratose.

(b) Wool fibers were heated under pressure in an autoclave by the use of saturated steam of 6 kg/cm² for 6 minutes and were abruptly released in the air to obtain a porous swollen matter. Ten grams of the swollen matter which had been reduced to pieces, 250 g of formic acid and 50 g of a 30% aqueous hydrogen peroxide solution were charged into a 500 ml three neck flask to immerse the pieces at room temperature for 1 day, whereupon no powder was found in the solution with the foam-like matter being floated on the upper layer. This reaction mixture was filtered and the filtrate was poured into 1.5 liters of water, followed by adding hydrochloric acid to adjust the pH to 4. The resulting precipitate was collected by filtration and washed with 500 ml of water to obtain 4.5 g of α-keratose. To the insoluble matter from which the reaction product had been removed by filtration were added 350 ml of water and then an ammoniacal solution to adjust the pH to 11, and the matter was immersed at room temperature for 1 day. The system was filtered and the filtrate was added with hydrochloric acid to make the pH a 4. The resulting precipitate was collected by filtration to obtain 0.7 g of α-keratose. It was found that 1.4 g of the insoluble matters was primarily made of β-keratose.

REFERENCE 2

Preparation of reduction decomposition derivatives of keratin materials:

(a) Ten grams of wool fibers were immersed in 600 ml of an aqueous solution with concentrations of 8M urea and 0.01M Tris buffer, to which was added 6 ml of 2-mercaptoethanol, followed by adjusting the pH to 10 by means of a 5N potassium hydroxide aqueous solution to conduct the reduction reaction in nitrogen atmosphere at room temperature. About 3 hours after commencement of the reaction, in the reaction solution 85% of the wool was dissolved. While the system was adjusted with a 5N potassium hydroxide aqueous solution so as not to permit the pH below 7, 16.5 g of iodoacetic acid was gradually added and the pH of the system was finally adjusted to 8.5 to carry out the carboxymethylation reaction at room temperature for 2 hours. The reaction solution was filtered to remove insoluble matters therefrom and the resultant filtrate was charged into a cellulose tube wherein it was dialyzed against ion-exchanged water to remove low molecular weight impurities including urea. As the urea was dialyzed, the content in the cellulose tube was turned white since water insoluble HGT (component with high contents of glycine and tyrosine) precipitated. After completion of the dialysis, the HGT was removed by centrifugal separation and S-carboxymethyl keratin (SCMKA) was obtained from the neutral transparent aqueous solution of SCMKA by the isoelectric precipitation method. That is, 1N hydrochloric acid was added to the system to adjust its pH to 4.4 by which SCMKA was turned insoluble and separated as precipitate. This precipitate was filtered, washed with ethanol and dried to obtain 4.2 g of SCMKA.

(b) The procedure of Reference 2-(a) was repeated except that there was used instead of wool fibers feathers which were heated for 6 minutes in an autoclave by means of superheated steam of 6 kg/cm² and 240° C. and then abruptly released in the air to obtain a porous swollen matter and that 1.75 g of maleic acid was used instead of iodoacetic acid, thereby obtaining 5.3 g of S-(1,2-dicarboxyethyl)-keratin.

(c) The procedure of Reference 2-(a) was repeated using a powder of hoof of horse instead of wool fibers and 11 g of acrylic acid instead of iodoacetic acid, thereby obtaining 4.2 g of S-(2-carboxyethyl)-keratin.

(d) The procedure of Reference 2-(a) was repeated using 28 g of styrenesulfonic acid instead of iodoacetic acid, thereby obtaining 4.8 g of S-(sulfophenylvinyl)-keratin.

(e) Eight grams of wool fibers were dispersed in 300 ml of n-propanol and 300 ml of a 0.1N Tris buffer solution. After substitution with nitrogen, 3.2 ml of tri-n-butylphosphine was added, followed by agitating at room temperature for 24 hours. After the solution was subjected to filtration, to the insoluble matter were added 400 ml of water, 9.28 g of maleic acid and about 30 ml of 5N potassium hydroxide to adjust the pH to 8.0, followed by agitating at room temperature for 6 hours. To the reaction system was added about 20 ml of a 28% aqueous ammoniacal solution to adjust the pH to 11.5, after which it was agitated at room temperature for 18 hours. The reaction solution was filtered to remove insoluble matters therefrom and the resultant filtrate was placed in a cellulose tube in which it was dialyzed against ion-exchanged water to remove low molecular weight impurities therefrom. After completion of the dialysis, the insoluble matters in the cellulose tube were removed by centrifugal separation and the neutral transparent aqueous solution was adjusted to have a pH of 4.4 by addition of about 5.5 ml of 1N hydrochloric acid and the resulting precipitate was collected by filtration, followed by washing with ethanol and drying to obtain 3.9 g of S-(1,2-dicarboxyethyl)-keratin.

(f) The procedure of Reference 2-(e) was repeated except that there was used instead of wool fibers a powder of a porous swollen matter which was obtained by heating wool in an autoclave by means of saturated steam of 6 kg/cm² for 6 minutes and that 16.5 g of 2-acrylamido2-methylpropanesulfonic acid was used instead of maleic acid, thereby obtaining 4.5 g of keratin-S-(2-acrylamido2-methylpropane-sulfonic acid).

REFERENCE 3

Preparation of Hydrolysis derivatives of Keratin materials:

(a) Ten grams of wool fibers were immersed in 300 g of a 1% sodium hydrogensulfite aqueous solution, whose pH was then adjusted to 6.7 by means of a 5N aqueous caustic soda solution. Thereafter, 0.2 g of papain was added to the system to conduct the hydrolysis reaction at 60° C. for 15 hours, by which about 80% of the wool was allowed to dissolve in. Insoluble matters were removed by filtration and the sulfite contained in the resultant filtrate was removed by the use of a membrane with a fractional molecular weight of 500. The aqueous solution of the hydrolysate was concentrated and freeze dried to obtain 7.7 g of the hydrolysate having a molecular weight of 500–2000.

(b) Ten grams of wool fibers were immersed in 300 g of a 75% phosphoric acid aqueous solution and the hydrolysis reaction was conducted at 120°–130° C. for 5 hours. The reaction system was cooled and filtered to remove insoluble matters therefrom, to which was added water of 4–5 times in volume of the filtrate to further remove insoluble matters. Then, calcium carbonate or barium hydroxide was added to the filtrate to adjust its pH to 6.7, after which the resulting precipitate was collected by filtration and dried to obtain 8.0 g of a hydrolysate having a molecular weight of 500–2000.

Note: The amount of S—S bonds in the hydrolysate obtained by the procedure of Reference 3-(a) or 3-(b) was 50 moles per $10^5$ g of the hydrolysate, revealing that little or no cystine in the wool was destroyed during the course of the hydrolysis.

(c) One hundred grams of feather were heated under pressure in an autoclave for 6 minutes by the use of superheated steam of 6 kg/cm$^2$ and 240° C., and then abruptly released in the air to obtain a porous swollen matter. This matter was reduced into pieces, to which was added 3 l of 0.3N caustic soda for conducting the hydrolysis reaction at 60° C. for 18 hours, followed by neutralizing with 1N hydrochloric acid and filtering the reaction solution. The sodium chloride in the resulting filtrate was removed by the ultrafiltration method using a membrane with a fractional molecular weight of 500. The aqueous solution of the hydrolysate of the keratin was concentrated and freeze dried to obtain 7.2 g of the hydrolysate of keratin. The molecular weight of the hydrolysate was found to be 1,800 when determined by the gel filtration method.

(d) 100 g of pieces of horse hoof with a uniform size of 0.25–1 mm were defatted with 50% methanol and 50% chloroform solutions and then treated with 1% ammoniacal solution to remove soluble proteins therefrom, which was then placed in a three neck flask, followed by adding 20 g of sodium hydroxide and 400 g of deionized water and subjecting to the hydrolysis reaction at 90° C. for 4 hours while agitating. After cooling, hydrochloric acid was added to adjust the pH of the system to 8 and then the reaction solution was filtered. The sodium chloride in the filtrate was removed, followed by repeating the procedure of Reference 3-(c) to obtain 68 g of a hydrolystate of keratin. This hydrolysate had a molecular weight of 2,500 when measured by the gel filtration method.

EXAMPLE 1

Hair rinse compositions of the following formulations were prepared and evaluated by a panel of ten persons. The results are shown in Table 1.

Formulation

| | |
|---|---|
| Distearyldimethylammonium chloride | 2.0% |
| Monocetyltrimethylammonium chloride | 1.0 |
| Cetyl alcohol | 1.0 |
| Decomposition derivative of keratin (Table 1) | 1.0 |
| Glycine | 0.4 |
| Water | Balance |

Evaluation Method:

Five hundred ml of 1:50 dilution of each of the hair rinse compositions and commercially available hair rinses were used to treat hair therewith and the thus treated hair was rinsed twice with hot water and air dried. The softness, smoothness and easiness for combing of the dried hair were sensorially assessed in comparison with commercially available rinses, in which indicated by ⊚ are sensorial characteristics which are superior to those of the commercially available hair rinses, by ○ are better characteristics, by Δ are equal characteristics, and by x are inferior characteristics.

TABLE 1

| Decomposition Derivatives of Keratin | Softness | Smoothness | Easiness for Combing |
|---|---|---|---|
| Derivative obtained in Reference 1-(a) | ⊚ | ⊚ | ⊚ |
| Derivative obtained in Reference 1-(b) | ⊚ | ⊚ | ⊚ |
| Derivative obtained in Reference 2-(a) | ⊚ | ⊚ | ⊚ |
| Derivative obtained in Reference 2-(b) | ⊚ | ⊚ | ⊚ |
| Derivative obtained in Reference 2-(c) | ⊚ | ⊚ | ⊚ |
| Derivative obtained in Reference 2-(d) | ⊚ | ⊚ | ⊚ |
| Derivative obtained in Reference 2-(e) | ⊚ | ⊚ | ⊚ |
| Derivative obtained in Reference 2-(f) | ⊚ | ⊚ | ⊚ |
| Derivative obtained in Reference 3-(a) | ○ | ○ | ⊚ |
| Derivative obtained in Reference 3-(b) | ○ | ○ | ⊚ |
| Derivative obtained in Reference 3-(c) | ○ | ○ | ⊚ |
| Derivative obtained in Reference 3-(d) | ○ | ○ | ⊚ |
| Comparative product | | | |
| Product obtained by decomposition of collagen with acid (M.W. 10,000–20,000) | Δ | Δ | Δ |
| Product obtained by decomposition of collagen with alkali (M.W. 10,000–20,000) | Δ | Δ | Δ |

EXAMPLE 2

Hair rinses of the following formulations were prepared and 50 ml of a 1:50 dilution of each rinse was used to treat 10 g of a tress, followed by rinsing twice with warm water. The tress was towel-dried with or without subsequent air drying and the melt and dry tresses were subjected to the measurement of combing force using a strain gauge. The results are shown in Table 2.

Formulation:

| | |
|---|---|
| Distearyldimethylammonium chloride | 2.0(%) |
| Cetyl alcohol | 1.0 |
| Decomposition derivative of keratin material in Reference 1-(a) | (Table 2) |
| 2-Amino-2-methylpropanol | 50% of the decomposition derivative of keratin material |
| Propylene glycol | 5 |
| Water | Balance |

Results:

TABLE 2

| Decomposition Derivative of Keratin Material (amount) | Wet state (g) | Dry state (g) |
|---|---|---|
| 0% | 380 | 280 |
| 0.01 | 320 | 180 |
| 0.1 | 300 | 170 |
| 1.0 | 270 | 160 |
| 5 | 250 | 155 |
| 15 | 260 | 160 |

EXAMPLE 3

Hair rinse compositions of the following formulations were prepared and 500 ml of 1:50 dilution of each hair rinse composition was used to treat hair therewith, followed by rinsing twice with warm water and air drying. The thus treated hair was evaluated in five grades by the Scheffe's pairs comparison method using a panel of 20 members with the results shown in Table 3.

Formulation:

| (A) | Distearyldimethylammonium chloride | 2.0(%) |
|---|---|---|
|  | Monostearyltrimethylammonium chloride | 0.5 |
|  | Decomposition derivative of keratin material in Reference 2-(a) | 0.05 |
|  | Water | Balance |
| (B) | Distearyldimethylammonium chloride | 2.0(%) |
|  | Monostearyltrimethylammonium chloride | 0.5 |
|  | Alkali hydrolysate of collagen (M.W. 800–1,000) | 0.05 |
|  | Water | Balance |
| (C) | Distearyldimethylammonium chloride | 2.0(%) |
|  | Monostearyltrimethylammonium chloride | 0.5 |
|  | Water | Balance |

Results:

TABLE 3

| Test Item | Inventive Composition | Good | Fair | Hard to say which | Fair | Good | Comparative Composition |
|---|---|---|---|---|---|---|---|
| Softness | (A) | 2 | 16 | 2 | 2 | 0 | (B) |
| Smoothness |  | 3 | 12 | 4 | 1 | 0 |  |
| Easiness of combing |  | 2 | 10 | 6 | 2 | 0 |  |
| Softness | (A) | 6 | 11 | 2 | 1 | 0 | (C) |
| Smoothness |  | 7 | 9 | 3 | 1 | 0 |  |
| Easiness of combing |  | 6 | 9 | 4 | 1 | 0 |  |

What is claimed is:

1. A hair rinse composition comprising
   (a) 0.01 to 10 wt. % of at least one cationic surface active agent, and
   (b) 0.1 to 5 wt. % of a hydrolysate of keratin material containing large amounts of disulfide bonds dispersed or dissolved in at least one solvent selected from the group consisting of water, ethyleneglycol and propylene glycol; wherein said hydrolysate of keratin material is obtained by hydrolyzing keratin material with an acid, alkali or enzyme, and has a molecular weight of 200 to 5,000.

2. A rinse composition according to claim 1, wherein the cationic surface active agent is a quarternary ammonium salt represented by the general formula (I)

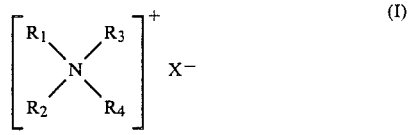

(in which one or two of $R_1$, $R_2$, $R_3$ and $R_4$ represent a long chain alkyl group or long chain hydroxyalkyl group having 8 to 20 carbon atoms, the others represent an alkyl group or hydroxyalkyl group having 1 to 3 carbon atoms, or a benzyl group, and X represents a halogen atom or an alkylsulfate having 1 to 2 carbon atoms).

* * * * *